United States Patent
Rozow, III et al.

[11] Patent Number: 6,090,146
[45] Date of Patent: Jul. 18, 2000

[54] FASTENER FOR A MODULAR IMPLANT

[75] Inventors: Stephen Rozow, III, Milford; Richard L. Renz, North Manchester, both of Ind.

[73] Assignee: Bristol-Myers Squibb Company, New York, N.Y.

[21] Appl. No.: 09/334,402

[22] Filed: Jun. 16, 1999

[51] Int. Cl.[7] .............................. A61F 2/32; F16B 39/28
[52] U.S. Cl. ................................. 623/22.42; 623/20.15; 411/290
[58] Field of Search ................................. 623/16, 18, 19, 623/20, 23; 411/291, 280, 290

[56] References Cited

U.S. PATENT DOCUMENTS

| | | | |
|---|---|---|---|
| 2,391,712 | 12/1945 | King et al. | 411/291 |
| 3,067,740 | 12/1962 | Haboush | 128/92 |
| 3,265,109 | 8/1966 | Hanfland | 411/291 |
| 5,080,685 | 1/1992 | Bolesky et al. | 623/23 |
| 5,330,535 | 7/1994 | Moser et al. | 623/20 |
| 5,405,396 | 4/1995 | Heldreth et al. | 623/20 |
| 5,456,719 | 10/1995 | Keller | 623/11 |
| 5,662,443 | 9/1997 | Dziaba | 411/291 |

*Primary Examiner*—David J. Isabella
*Attorney, Agent, or Firm*—Cary R. Reeves

[57] ABSTRACT

A joint between an implant body component and a stem component provides an initially rigid connection that further remains rigid even if the joint settles upon being loaded. The body and stem have portions comprising a male/female taper junction. A fastener maintains the taper junction in tight engagement. The fastener engages the implant components and draws them together. The fastener includes a resilient portion that deflects such that if settling occurs, the resilient portion maintains compressive contact between the fastener and the components.

8 Claims, 2 Drawing Sheets

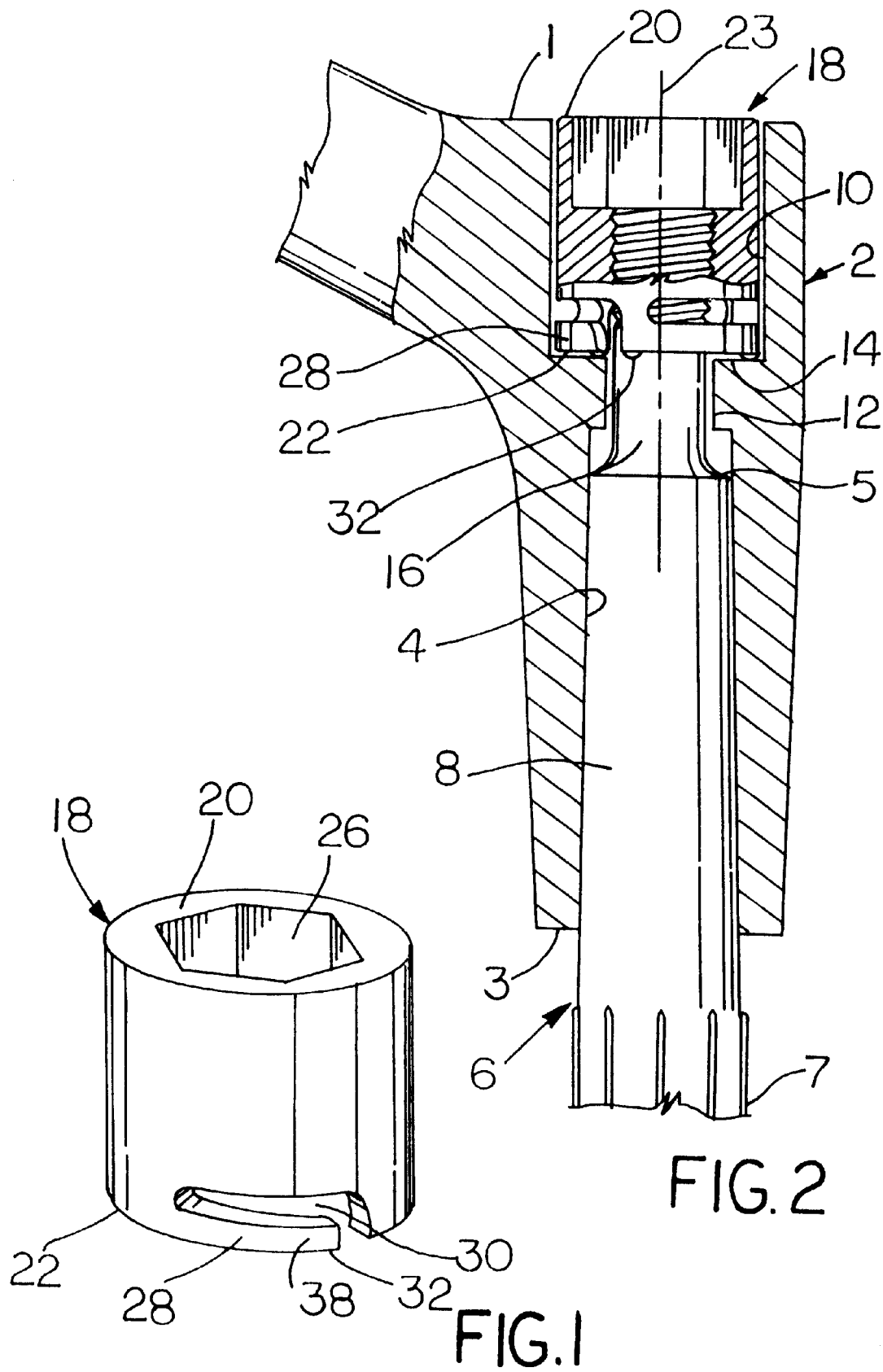

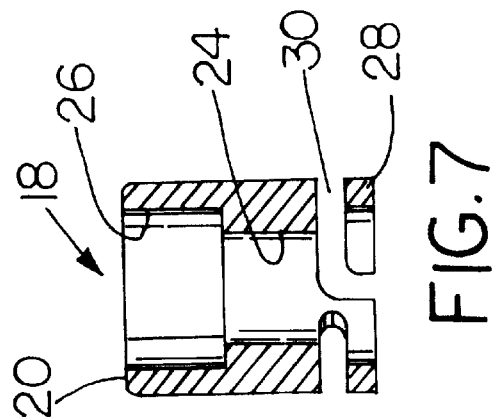
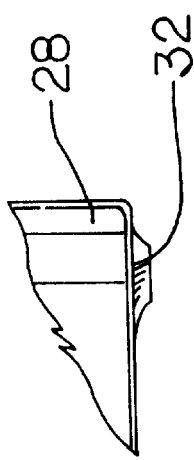
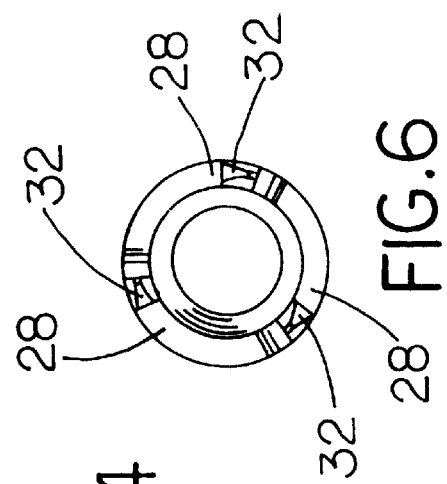
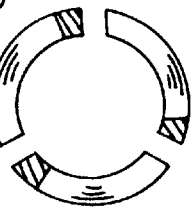
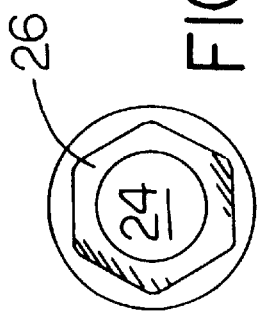
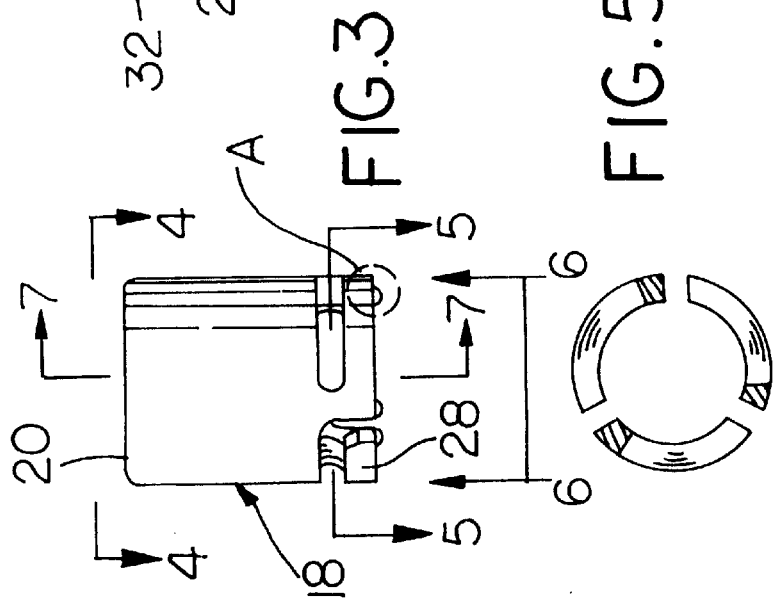

FASTENER FOR A MODULAR IMPLANT

BACKGROUND OF THE INVENTION

The present invention relates to connections for modular orthopaedic implants. More particularly, the present invention relates to a male/female taper connection including a fastener that maintains compression on a male/female taper junction even if the junction settles.

Many orthopaedic implants comprise a body and a stem connectable to the body. The connection between the body and stem is commonly provided by mating tapers on the body and stem. For example, U.S. Pat. No. 5,405,396 teaches a tibial prosthesis comprising a plate and a stem connectable with the plate. The plate includes a female taper and the stem includes a male taper for close fitting within the female taper. In another example, U.S. Pat. No. 3,067,740 ('740) teaches a hip joint prosthesis comprising a socket member, or upper body, and a nail, or stem member. The upper body includes a female taper and the stem includes a male taper for close fitting within the female taper. The upper end of the stem is threaded to receive a cap nut for compressing the upper body and stem into firm engagement. Such prior art tapers can be of a self-locking variety in which case a locking screw or cap nut may be used to reinforce the self-locking feature, or the tapers can be non-self-locking in which case a locking screw or cap nut is necessary to provide locking. One problem with prior taper joints is that the taper can settle after initial assembly, such as when it is loaded by patient activities. The locking screw may then lose compressive contact with the joint and may even begin to unscrew from the implant. The '740 patent teaches the use of a resilient locking plug to prevent the nut from unscrewing by providing a frictional engagement between the threads of the cap nut and the stem. However, this arrangement does nothing to address the loss of compressive contact that would occur during settling. In addition, the use of a resilient material introduces another material into the prosthesis that may be undesirable.

SUMMARY OF THE INVENTION

The present invention provides a connecting joint between an implant body component and a stem component that provides an initially rigid connection that further remains rigid even if the joint settles upon being loaded. The body and stem have portions comprising a male/female taper junction. A fastener maintains the taper junction in tight engagement. The fastener engages the implant components and draws them together. The fastener includes a resilient portion that deflects such that if settling occurs, the resilient portion maintains compressive contact between the fastener and the components.

BRIEF DESCRIPTION OF THE DRAWINGS

FIG. 1 is a perspective view of a fastener in accordance with the present invention.

FIG. 2 is a side sectional view of the fastener of FIG. 1 assembled with a body and stem component in accordance with the present invention.

FIG. 3 is a side plan view of the fastener of FIG. 1.

FIG. 4 is a top plan view of the fastener of FIG. 1.

FIG. 5 is a section view of the fastener of FIG. 1 taken along line 5—5 of FIG. 3.

FIG. 6 is a bottom plan view of the fastener of FIG. 1.

FIG. 7 is a side sectional view of the fastener of FIG. 1.

FIG. 8 is an enlarged partial view of the area indicated by the letter "A" in FIG. 3.

DETAILED DESCRIPTION OF THE INVENTION

FIGS. 1–8 depict an exemplary modular hip joint prosthesis comprising two components joined by male/female engaging portions. An implant body 2 has a proximal end 1 and a distal end 3. Preferably, the body 2 includes a female taper 4 open at the distal end 3 and narrowing toward the proximal end 1. The body 2 further includes a recess 10 opening to the proximal end and a through bore 12 communicating between the female taper 4 and the recess 10. The recess 10 is wider than the through bore 12 so that a shoulder 14 is formed in the body 2 opposite the female taper 4. In another embodiment (not shown), the recess 10 is omitted and the through bore 12 communicates from the female taper 4 to the proximal end 1, the proximal end 1 surface forming the shoulder.

An implant stem 6 has a proximal end 5 and a distal end 7. Preferably, the stem 6 includes a male taper 8 near its proximal end 5. The male taper 8 narrows toward the proximal end 5 for engagement with the female taper 4. Preferably the taper angles are chosen such that the male 8 and female 4 tapers are self-locking upon being impacted into engagement as is known in the art. The stem 6 preferably includes a threaded stud 16 extending from its proximal end 5. The stud 16 is sized to extend through the through bore 12 when the stem 6 and body 2 are assembled together.

A fastener 18 includes a proximal end 20 and a distal end 22 and a longitudinal axis 23. A threaded bore 24 opens toward the distal end 22 and is sized to thread onto the threaded stud 16. The proximal end 20 includes a driving portion 26 for receiving a wrench. Preferably, it is a hexagonal recess, as shown, for receiving a hexagonal wrench. In an alternative embodiment, the stem includes a threaded bore and the fastener includes a threaded stud extending from its distal end, the threaded stud being sized to threadably engage the threaded bore.

Slots 30 are formed circumferentially in the distal end 22 and open distally to define spring tabs 28. Spring tabs 28 thus form cantilevered circumferential extensions that are resiliently deflectable proximally-distally, or in other words, in a direction along the longitudinal axis 23. A protrusion 32 extends distally near the free end 34 of each spring tab 28. The exemplary embodiment shows a small bump machined on the spring tabs 28 and protruding distally. The protrusions 32 are the distal most aspects of the fastener 18, as shown in FIG. 3, such that if the fastener 18 is rested on a flat surface the protrusions 32 will be in contact with the surface. In an alternative embodiment the spring tabs are formed without the protrusions 32 but are instead permanently bent distally so that the free ends 34 are the distal most aspects of the fastener 18.

In use, the male taper 8 is inserted into the female taper 4 with the threaded stud 16 extending through the through bore 12 into the recess 10. The tapers are then seated firmly. Seating may be facilitated by impacting the parts together, such as with a mallet. The fastener 18 is threaded onto the threaded stud 16 until the spring tabs 28 contact the shoulder 14. At this point, further tightening of the fastener 18 results in elastic bending of the spring tabs 28 proximally. Preferably the fastener 18 is tightened to a measured predetermined torque so that the spring tabs 28 are deflected a desired reproducible amount. Thus assembled, the taper joint is well seated and held in compression with the spring tabs being biased toward the shoulder by stored spring energy. Frictional forces between the spring tabs 28 and the shoulder 14 resist unthreading of the fastener 18. If the joint settles during loading of the implant, such as by patient activity including walking, the spring tabs 28 will move toward the shoulder due to spring tension and maintain the joint in compression. Since the spring tabs 28 remain biased against the shoulder 14, friction still acts to resist unthreading of the fastener 18.

It will be understood by those skilled in the art that the foregoing has described a preferred embodiment of the present invention and that variations in design and construction may be made to the preferred embodiment without departing from the spirit and scope of the invention defined by the appended claims.

What is claimed is:

1. A modular orthopaedic implant comprising:

a stem with a tapered portion having a longitudinal axis;

a body with a tapered portion configured for engagement with the stem tapered portion; and a threaded fastener for drawing the stem and body tapered portions into engagement along the longitudinal axis, the fastener having first and second ends, the fastener having a spring element extending from one end, the fastener threadably engaging the stem, the spring element bearing against and being resiliently biased against the body along the longitudinal axis.

2. The modular orthopaedic implant of claim 1 wherein, the stem and body tapers are self-locking.

3. The modular orthopaedic implant of claim 2 wherein, the stem has a male taper and the body has a female taper.

4. The modular orthopaedic implant of claim 3 wherein, the fastener has a recessed driving portion in an end opposite the spring element.

5. A modular hip prosthesis for insertion into the intramedullary canal of a femur and replacing the head of a said femur, the prosthesis comprising:

a stem for insertion into a said intramedullary canal of a said femur, the stem having a proximal end and a distal end, the stem having a male tapered portion near its proximal end and a threaded stud extending proximally from the tapered portion;

a body for replacing a said head of a said femur, the body having a proximal end and a distal end, the body having a female tapered portion engaging the stem male tapered portion, the body having a through bore communicating between the female tapered bore and the distal end of the body, the threaded stud extending into the through bore; and a fastener for drawing the stem and body tapered portions into engagement, the fastener having proximal and distal ends and a longitudinal axis extending between the proximal and distal ends, the proximal end including a driver engaging portion, the distal end including a circumferential slot opening distally to form a cantilevered circumferential extension, the extension being resiliently deflectable proximally-distally, the fastener threadably engaging the threaded stud, the extension bearing against and being resiliently biased against the proximal end of the body.

6. A fastener for drawing a plurality of modular orthopaedic implant components together, the, fastener comprising a member having a first end, a second end, and a longitudinal,axis extending between the first and second ends, a spring tab extending from one of the first and second ends, the spring tab bearing against one of the components and being elastically deflected in a direction along the longitudinal axis, the spring tab biasing the components together along the longitudinal axis such that when the components settle into more closely spaced relation, the spring tab elastically recovers to maintain its bearing relationship against one of the components.

7. The fastener of claim 1 wherein the member has a female thread for engaging a male thread on one of said components.

8. The fastener of claim 1 wherein the spring tab is a cantilevered circumferential extension projecting from one of the first or second ends.

* * * * *